(12) United States Patent
Mata et al.

(10) Patent No.: US 10,405,958 B2
(45) Date of Patent: Sep. 10, 2019

(54) DEVICES AND METHODS FOR FIXATION OF BODILY IMPLANTS

(71) Applicant: Boston Scientific Scimed, Inc., Maple Grove, MN (US)

(72) Inventors: Vincent Mata, Monroe, CT (US); Jeffrey E. Ransden, Fairfield, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 224 days.

(21) Appl. No.: 14/674,923

(22) Filed: Mar. 31, 2015

(65) Prior Publication Data
US 2015/0282918 A1    Oct. 8, 2015

Related U.S. Application Data

(60) Provisional application No. 61/975,379, filed on Apr. 4, 2014.

(51) Int. Cl.
| *A61F 2/00* | (2006.01) |
| *A61B 17/068* | (2006.01) |
| *A61B 17/04* | (2006.01) |
| *A61B 17/064* | (2006.01) |
| *A61B 17/00* | (2006.01) |
| *A61B 17/30* | (2006.01) |

(52) U.S. Cl.
CPC ........ *A61F 2/0045* (2013.01); *A61B 17/0493* (2013.01); *A61B 17/068* (2013.01); *A61B 17/0644* (2013.01); *A61B 17/0684* (2013.01); *A61B 17/0482* (2013.01); *A61B 2017/00805* (2013.01); *A61B 2017/0409* (2013.01); *A61B 2017/0419* (2013.01); *A61B 2017/0464* (2013.01); *A61B 2017/0645* (2013.01); *A61B 2017/306* (2013.01)

(58) Field of Classification Search
CPC ....... A61M 25/0136; A61N 2005/1094; A61N 5/1016; A61J 15/0069; A61F 2002/2484; A61B 18/1492; A61B 1/00154; A61B 18/24

See application file for complete search history.

(56) References Cited

U.S. PATENT DOCUMENTS

| 6,478,791 | B1 | 11/2002 | Carter et al. |
| 8,109,867 | B2 | 2/2012 | Rosenblatt |
| 2007/0244490 | A1* | 10/2007 | Moehle ............... A61B 17/282 606/108 |
| 2007/0293717 | A1 | 12/2007 | Kaleta et al. |
| 2009/0149700 | A1 | 6/2009 | Garcia et al. |
| 2010/0191262 | A1 | 7/2010 | Harris et al. |
| 2012/0165602 | A1 | 6/2012 | Nissen |
| 2012/0253106 | A1 | 10/2012 | Khamis et al. |
| 2013/0079813 | A1 | 3/2013 | Li et al. |
| 2013/0204070 | A1* | 8/2013 | Makel ................. A61N 5/1016 600/3 |

FOREIGN PATENT DOCUMENTS

EP    2147641  B1    4/2013

* cited by examiner

*Primary Examiner* — Christine H Matthews
(74) *Attorney, Agent, or Firm* — Brake Hughes Bellermann LLP

(57) ABSTRACT

A medical device includes an elongate member configured to be at least partially disposed within a body of a patient. The elongate member has an outer surface. The outer surface of the elongate member has a first ridge and a second ridge.

14 Claims, 14 Drawing Sheets

DEVICES AND METHODS FOR FIXATION OF BODILY IMPLANTS

CROSS-REFERENCE TO RELATED APPLICATION

This application is a Nonprovisional of, and claims priority to, U.S. Patent Application No. 61/975,379, filed on Apr. 4, 2014, entitled "DEVICES AND METHODS FOR FIXATION OF BODILY IMPLANTS", which is incorporated by reference herein in its entirety.

TECHNICAL FIELD

This disclosure relates generally to medical devices and surgical procedures, and more particularly to medical devices and methods used to implant and attach bodily implants within a body of a patient.

BACKGROUND

Bodily implants, such as mesh implants, are sometimes placed within a body of a patient. For example, sometimes implants are placed within a body of a patient to provide support to portions of the body of the patient. Implants may be placed within a pelvic region of a patient to provide support to portions of the pelvic region of the patent.

In some procedures for placing implants within a body of a patient, an implant is anchored or secured to bodily tissue. In some cases, it is desirable to limit or to control the depth of penetration of the anchor or other device used to couple or attach the implant within the body of the patient. For example, in some sacral colpopexy procedures, an implant is coupled to an outer surface of a vaginal wall of a patient. It can be desirable to control or limit the depth of penetration of the anchor or other device used to couple the implant to the outer surface of the vaginal wall. For example, it can be desirable to prevent the anchor or other device use to couple or attach the implant from penetrating into the vagina (or otherwise penetrate completely through the vaginal wall).

Accordingly, there is a need for medical devices and methods that allow for effective and efficient implant placement. For example, there is a need for devices and methods that allow for or help control the depth of penetration of an anchoring mechanism used to couple or attach an implant within a body of a patient.

SUMMARY

In one embodiment, a medical device includes an elongate member configured to be at least partially disposed within a body of a patient. The elongate member has an outer surface. The outer surface of the elongate member has a first ridge and a second ridge.

In another embodiment, a medical device includes an elongate member and an expander. The expander defines a lumen and is slidably coupled to the elongate member. The expander has a proximal end portion and a distal end portion. The distal end portion of the expander has a tapered section.

In another embodiment, a method of placing an implant within a body of a patient includes inserting a manipulator within a vagina of a patient; disposing the implant adjacent a vaginal wall of the patient; moving a first portion of the manipulator with respect to a second portion of the manipulator to expand the vagina of the patient; and attaching the implant to the vaginal wall of the patient.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including"

and/or "having", as used herein, are defined as comprising (i.e., open transition). The term "coupled" or "moveably coupled," as used herein, is defined as connected, although not necessarily directly and mechanically.

In general, the embodiments are directed to systems, methods, and devices for placing implants within in body of a patient. For example, the systems, methods, and devices may be used in various types of procedures, such as procedures for treating female pelvic prolapse or anal prolapse in males or females. Also, the systems, methods, and devices described herein may be used in transabdominal and/or transvaginal procedures.

The term patient may hereafter be used for a person who benefits from the medical device or the methods disclosed in the present application. For example, the patient can be a person whose body is operated through the medical device or the method disclosed by the present invention. For example, in some embodiments, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1:
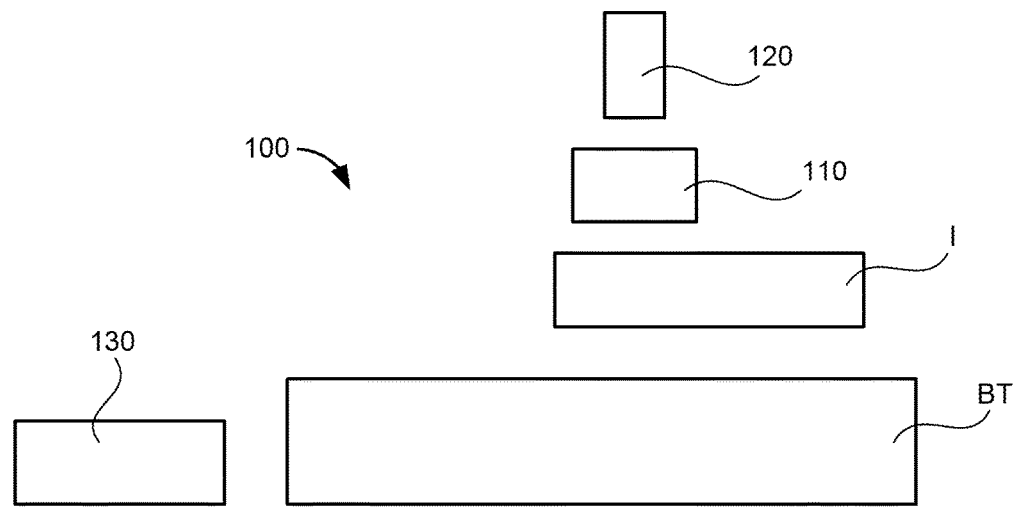
FIG. 1 is a schematic diagram of a system according to an embodiment of the invention.

FIG. 1 is a schematic diagram of a system 100 according to an embodiment of the invention. The system 100 may be used to couple or attach a bodily implant within a body of a patient. The system 100 includes an anchor or coupling member 110, an insertion device 120, and a manipulator 130.

The anchor or coupling member 110 is configured to engage a bodily implant I and help retain the bodily implant I in place within the body of the patient. In some embodiments, the anchor or coupling member 110 engages the bodily implant I and bodily tissue BT to retain the implant I in place within the body with respect to the bodily tissue BT. In some embodiments, the bodily tissue BT is tissue located in the pelvic region of a patient. For example, in some embodiments, the bodily tissue BT is a vagina or a vaginal wall of a patient. The implant I may be of any shape or size. In some embodiments, the implant I includes a mesh portion.

In some embodiments, the anchor or coupling member 110 includes a hook, barb, or extension portion that is configured to extend through the implant I and into the bodily tissue BT to couple or help couple the implant I to the bodily tissue BT. In other embodiments, the anchor or coupling member 110 is a suture or other type of coupling device.

In some embodiments, the anchor or coupling member 110 is configured to have a limited penetration depth into the bodily tissue BT. In some embodiments, the anchor or coupling member 110 is configured or sized to penetrate less than five millimeters (5 mm) of bodily tissue. In other embodiments, the anchor or coupling member 110 is configured to penetrate more than five millimeters (5 mm) of bodily tissue. In some cases the bodily tissue BT is a vagina or a vaginal wall of a patient. In some embodiments, the anchor or coupling member 110 is configured to couple the implant I to the vagina or the vaginal wall or tissue near the vaginal wall without extending through the vaginal wall into the vaginal canal of the patient.

The anchor or coupling member 110 may be formed of any type of biocompatible material. In some embodiments, the anchor or coupling member 110 may be formed of a bioresorbable material. In some embodiments, the system 100 may include more than one anchor or coupling member 110 to secure or couple the implant I within the body of the patient.

The insertion device 120 is configured to facilitate the placement of the anchor or coupling member 110 within the body of the patient. In some embodiments, the insertion device 120 is configured to engage the anchor 110 and insert the anchor 110 into position with the body of the patient. Once the anchor 110 is disposed in the appropriate location, the anchor 110 can be disengaged from the insertion device 120 and the insertion device 120 can be removed from the body of the patient.

In some embodiments, the insertion device 120 may be inserted into the body via an abdominal incision. In other embodiments, the insertion device 120 may be inserted into the body via other locations of the body, such as via a vaginal opening or a vaginal incision or other type of incision.

The manipulator 130 is configured to manipulate bodily tissue. In some embodiments, the manipulation of the tissue facilitates the placement or securement of the bodily implant I within the body of the patient. For example, in some embodiments, the manipulator 130 is configured to be inserted into the body of the patient and manipulate the bodily tissue BT so as to facilitate the securement of the bodily implant I to the bodily tissue BT.

In some embodiments, the manipulator 130 is configured to be inserted into a vagina of the patient and to manipulate the vaginal tissue or vaginal walls of the patient. In some cases, such manipulation of the vagina or the vaginal walls facilitates the placement of the implant in a correct location with respect the vagina and the securement of the implant to the vagina or tissue proximate the vagina via the anchor 110.

The manipulator 130 may be formed of any type of biocompatible material. The manipulator 130 may be configured to be inserted into any portion of the body of the patient and may be configured to be inserted into the body via any opening or incision.

Figure 2:
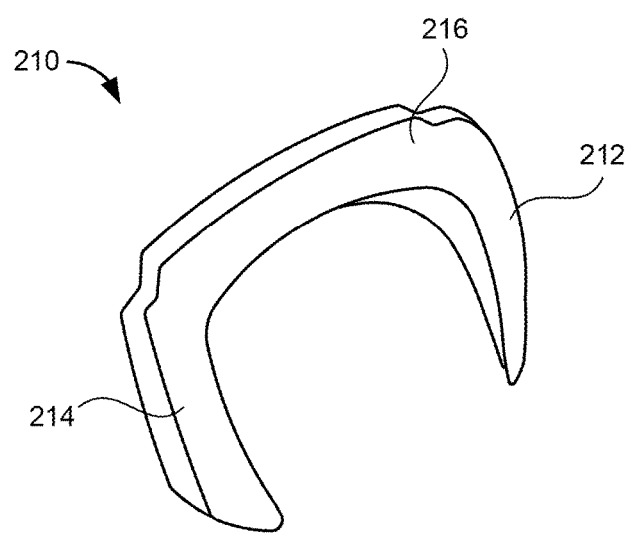
FIG. 2 is a perspective view of an anchor according to an embodiment of the invention.
Figure 3:
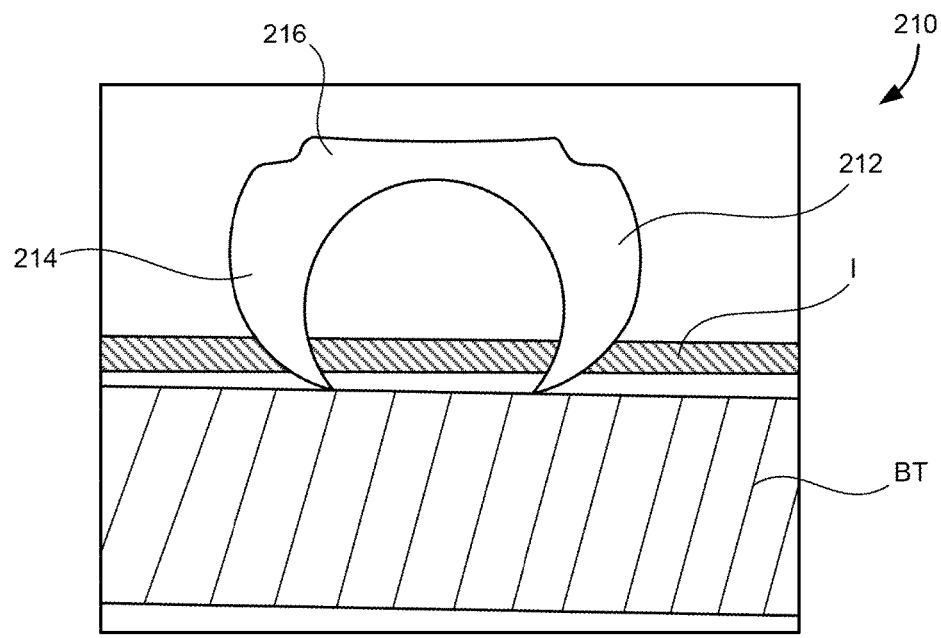
FIG. 3 is a side view of the anchor of FIG. 2 is an open configuration.
Figure 4:
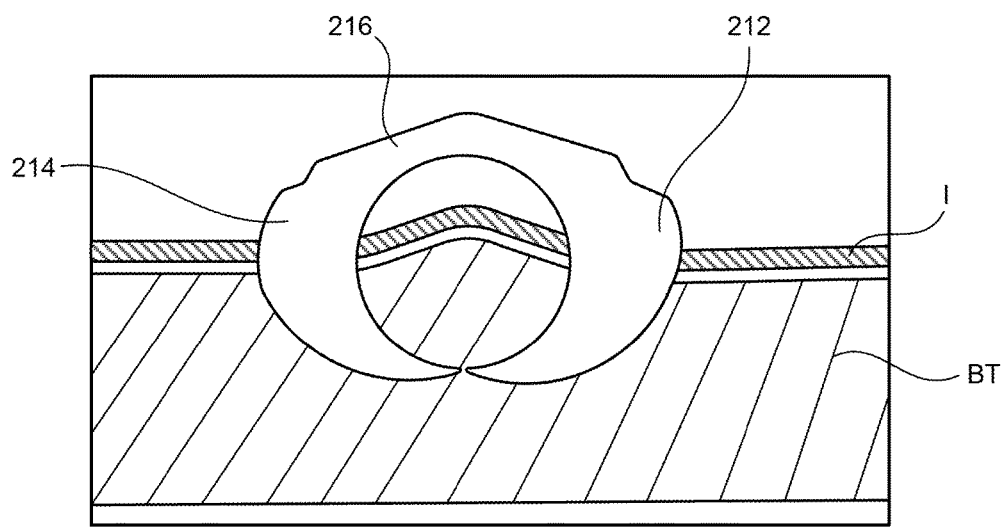
FIG. 4 is a side view of the anchor of FIG. 2 in a closed configuration.

FIGS. 2-4 illustrate an anchor or coupling member 210 in accordance with an embodiment of the invention. The anchor or coupling member 210 is configured to engage a bodily implant I and help retain the bodily implant I in place within the body of the patient. Specifically as best illustrated in FIG. 4, the anchor or coupling member 210 engages the bodily implant I and bodily tissue BT to retain the implant I in place within the body with respect to the bodily tissue BT. In some embodiments, the bodily tissue BT is tissue located in the pelvic region of a patient. For example, in some embodiments, the bodily tissue BT is a vagina or a vaginal wall of a patient.

In the illustrated embodiment, the anchor or coupling member 210 a base portion 216 and extension portions 212 and 214 that are configured to extend through the implant I and into the bodily tissue BT to couple or help couple the implant I to the bodily tissue BT. The extension portions 212 and 214 may be configured to move or bend with respect to the base portion 216. For example, the extension portion 212 and 214 may be configured to be inserted into the body and through the bodily tissue BT while the extension portions 212 and 214 are in a first position or configuration (as illustrated in FIG. 3). Once the anchor 210 is in place within the body, the extension portions 212 and 214 may move to a second position or configuration (as illustrated in FIG. 4).

Figure 5:
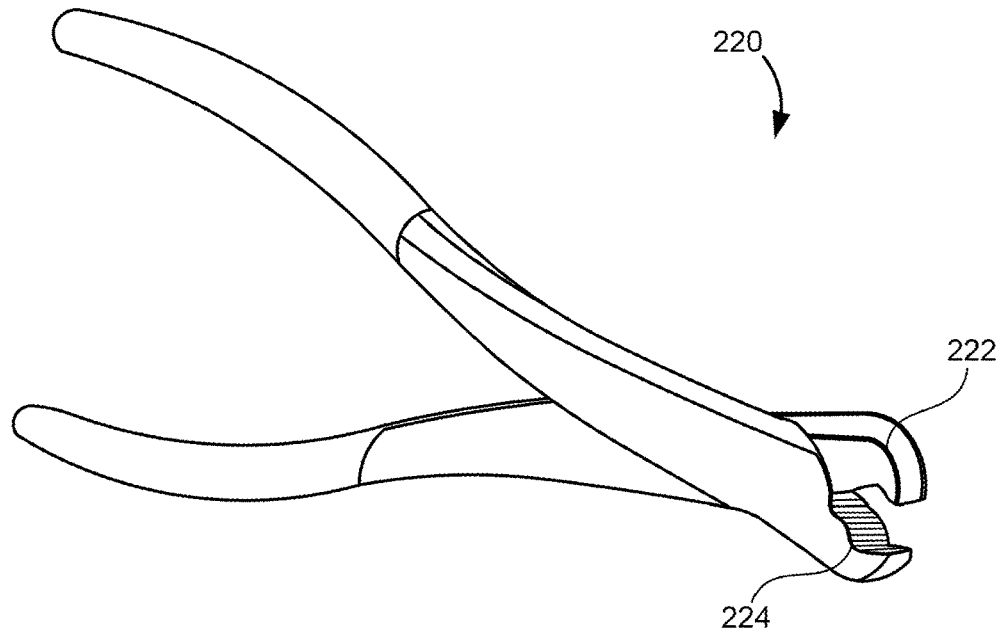
FIG. 5 is a perspective view of a device for delivering the anchor of FIG. 2 according to an embodiment of the invention.

In some embodiments, the anchor or coupling mechanism 210 may be inserted into the body of the patient using an insertion device 220 as illustrated in FIG. 5. The insertion device 220 may be configured to grasp or hold the anchor or coupling mechanism 210 while the insertion device 220 and the anchor 210 are inserted into the body of the patient. The insertion device 220 may be configured to then squeeze or crimp the anchor 210 into its second or closed position. For example, in some embodiments, the insertion device 220 may be configured to grasp the anchor 210 using grip portions 222 and 224 and squeeze the anchor 210 at or near the junction of the extension members 212 and 214 and the base portion 216 or on the extension members 212 and 214 themselves to move the extension members 212 and 214 to their second positions.

In other embodiments, a different type of device may be used to deliver the anchor 210 into position within the body of the patient. In some embodiments, the delivery device may be configured to retain or hold more than one anchor 210. In such embodiments, the delivery device and the plurality of anchors may be inserted into the body. One the anchors may be placed within the body at different locations and may be placed serially without having to remove the delivery device from the body of the patient.

In some embodiments, the anchor or coupling member 210 is configured to have a limited penetration depth into the bodily tissue BT. For example, in some cases the bodily tissue BT is a vagina or a vaginal wall of a patient. In some embodiments, the anchor or coupling member 110 is configured to couple the implant I to the vagina or the vaginal wall without extending through the vaginal wall into the vaginal canal of the patient. As best illustrated in FIG. 4, in the illustrated embodiment, extension portions 212 and 214 of the anchor 210 do not extend though the bodily tissue BT.

The anchor or coupling member 210 may be formed of any type of biocompatible material. For example, in some embodiments, the anchor 210 is formed of a material that may be bent or reshaped and is configured to hold the shape in which it is placed until it is changed. For example, in some embodiments, the anchor 210 may be placed such that the extension portions 212 and 214 are in their first positions or configurations and the anchor 210 will stay in such a position. The extension portions 212 and 214 may then be moved to their second positions or configurations and the anchor 210 will stay in such a position. In other embodiments, the anchor or coupling member 210 is formed of a shape memory material. In some embodiments, the anchor or coupling member 210 is formed of a material has a biased configuration (such as biasing the anchor or extension portions to one of the first position or second position).

Figure 6:
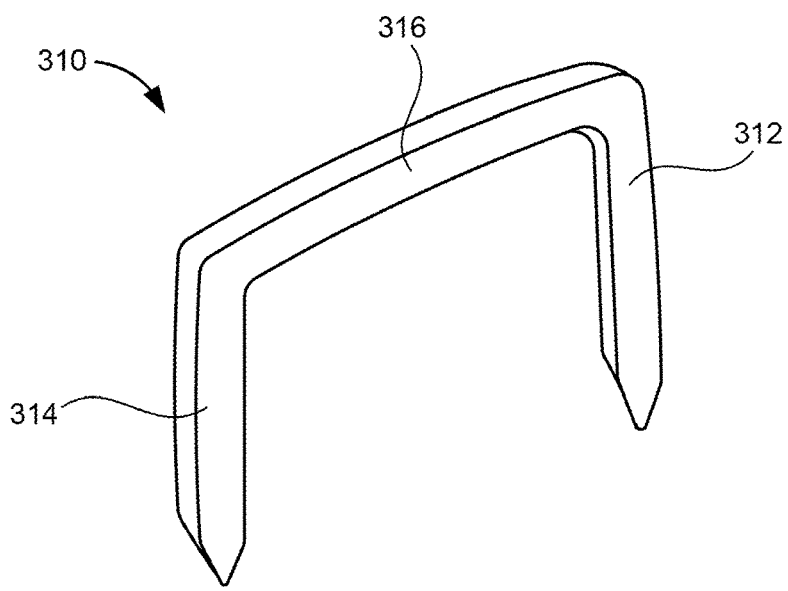
FIG. 6 is a perspective view of an anchor according to an embodiment of the invention.
Figure 7:
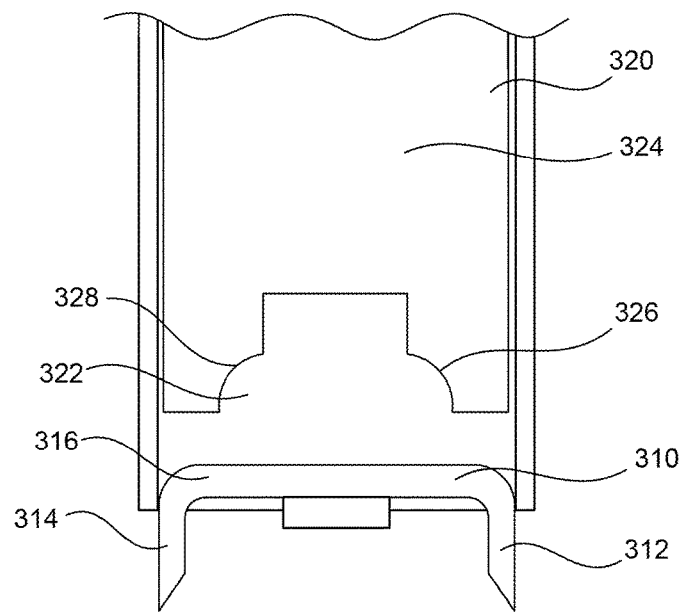
FIG. 7 is a side view of the anchor of FIG. 6 in an open configuration.
Figure 8:
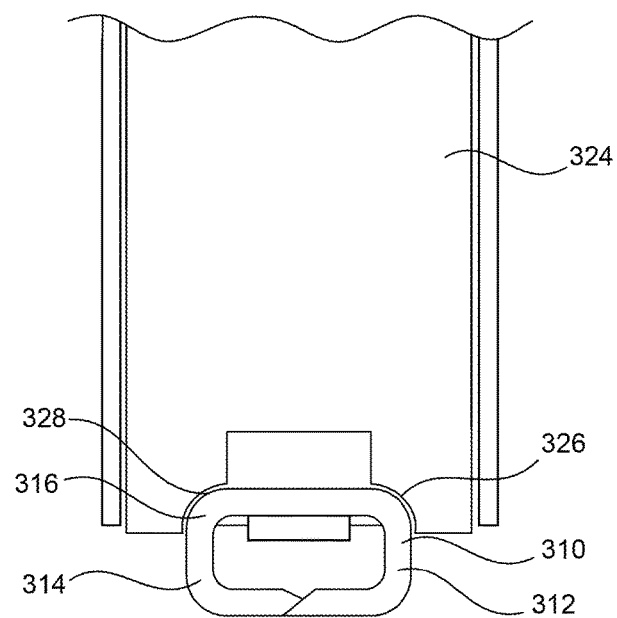
FIG. 8 is a side view of the anchor of FIG. 6 in a closed configuration.

FIGS. 6-8 illustrate an anchor or coupling member 310 in accordance with an embodiment of the invention. FIGS. 7 and 8 illustrate the anchor or coupling member 310 along with a portion of a insertion or delivery device 320 (as described in more detail below) shown see-though so as to show the internal components. The anchor or coupling member 310 is configured to engage a bodily implant and help retain the bodily implant in place within the body of the patient. Specifically, the anchor or coupling member 310 engages the bodily implant and bodily tissue to retain the implant in place within the body with respect to the bodily tissue. In some embodiments, the bodily tissue is tissue located in the pelvic region of a patient. For example, in some embodiments, the bodily tissue is a vagina or a vaginal wall of a patient.

In the illustrated embodiment, the anchor or coupling member 310 a base portion 316 and extension portions 312 and 314 that are configured to extend through the implant and into the bodily tissue to couple or help couple the implant to the bodily tissue. The extension portions 312 and 314 may be configured to move or bend with respect to the base portion 316. For example, the extension portion 312 and 314 may be configured to be inserted into the body and through the bodily tissue while the extension portions 312 and 314 are in a first position or configuration (as illustrated in FIG. 7). Once the anchor 310 is in place within the body, the extension portions 312 and 314 may move to a second position or configuration (as illustrated in FIG. 8).

Figure 9:
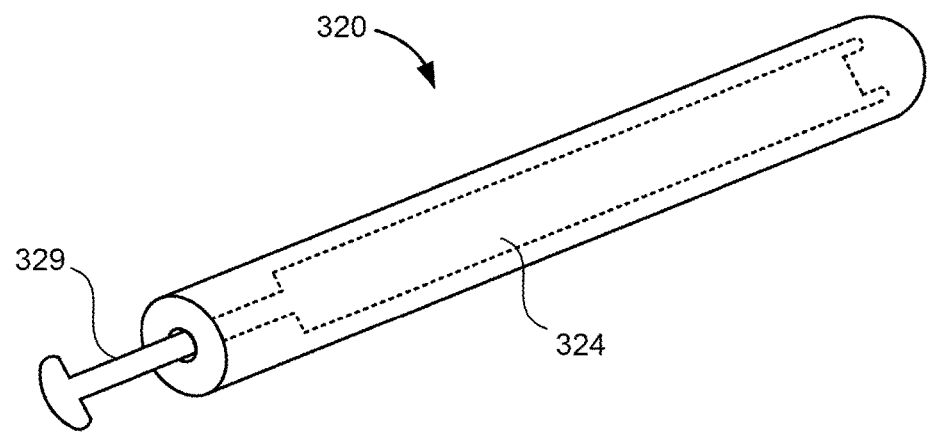
FIG. 9 is a perspective view of a device for delivering the anchor of FIG. 10.

In some embodiments, the anchor or coupling mechanism 310 may be inserted into the body of the patient using an insertion device 320 as illustrated in FIG. 9 (and partially illustrated in FIGS. 7 and 8). The insertion device 320 may be configured to retain the coupling mechanism 310 within a lumen 322 defined by the insertion device 320 while the insertion device 320 and the anchor 310 are inserted into the body of the patient. The insertion device 320 may be configured to then push or force the anchor 310 out of the lumen 322. For example, in the illustrated embodiment, a pusher 324 may be moved by the operator or physician (such as via the actuator 329 extending from a proximal end portion of the insertion device 320), to force or push the anchor 310 out of the lumen 322. In the illustrated embodiment, the pusher 324 is shaped such that it is configured to force or cause the extension portions 312 and 314 into their second position (as illustrated in FIG. 8). Specifically, the pusher 324 includes engagement portions 326 and 328 that are configured to contact the anchor 310 and cause the extension portions 312 and 314 to move to their second positions.

In other embodiments, a different type of device may be used to deliver the anchor 310 into position within the body of the patient. In some embodiments, the delivery device may be configured to retain or hold more than one anchor 310. In such embodiments, the delivery device and the plurality of anchors may be inserted into the body. The anchors may be placed within the body at different locations and may be placed serially without having to remove the delivery device from the body of the patient.

In some embodiments, the anchor or coupling member 310 is configured to have a limited penetration depth into the bodily tissue. For example, in some cases the bodily tissue is a vagina or a vaginal wall of a patient. In some embodiments, the anchor or coupling member 310 is configured to couple the implant to the vagina or the vaginal wall without extending through the vaginal wall into the vaginal canal of the patient.

The anchor or coupling member 310 may be formed of any type of biocompatible material. Specially, in some embodiments, the anchor or coupling member 310 is formed of titanium. In some embodiments, the anchor 310 is formed of a material that may be bent or reshaped and is configured to hold the shape in which it is placed until it is changed. For example, in some embodiments, the anchor 310 may be placed such that the extension portions 312 and 314 are in their first positions or configurations and the anchor 310 will stay in such a position. The extension portions 312 and 314 may then be moved to their second positions or configurations and the anchor 310 will stay in such a position. In other embodiments, the anchor or coupling member 310 is formed of a shape memory material. In some embodiments, the anchor or coupling member 310 is formed of a material has a biased configuration (such as biasing the anchor or extension portions to one of the first position or second position).

Figure 10:
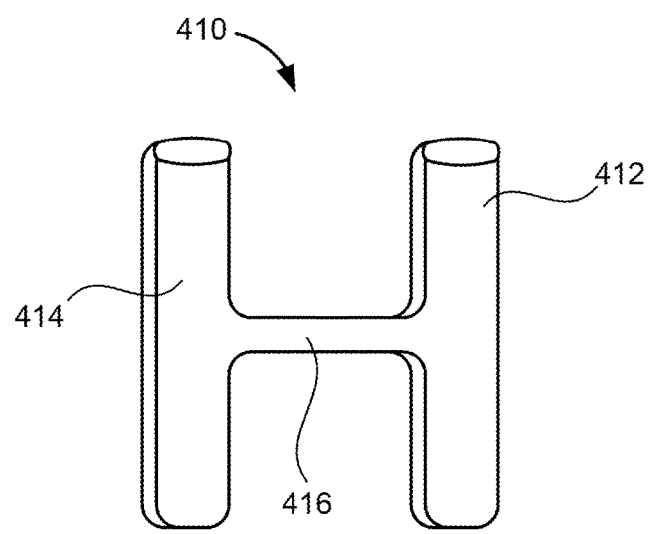
FIG. 10 is a perspective view of an anchor according to an embodiment of the invention.
Figure 11:
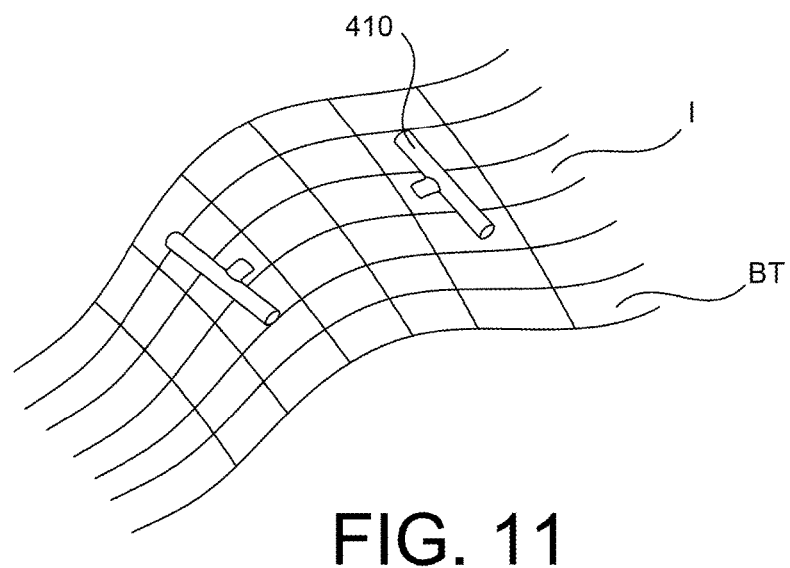
FIG. 11 is a schematic illustration of an anchor of FIG. 10 disposed within a body of a patient.

FIGS. 10 and 11 illustrate an anchor or coupling member 410 in accordance with an embodiment of the invention. The anchor or coupling member 410 is configured to engage a bodily implant and help retain the bodily implant in place within the body of the patient. Specifically, the anchor or coupling member 410 engages the bodily implant I and bodily tissue BT to retain the implant in place within the body with respect to the bodily tissue BT. In some embodiments, the bodily tissue BT is tissue located in the pelvic region of a patient. For example, in some embodiments, the bodily tissue BT is a vagina or a vaginal wall of a patient.

In the illustrated embodiment, the anchor or coupling member 410 a base portion 416 and retention portions 412 and 414. The base portion 416 is configured to extend through the implant and into the bodily tissue and the retention portions 412 and 414 are configured to help retain the anchor 410 in place within the body of the patient.

Figure 12:
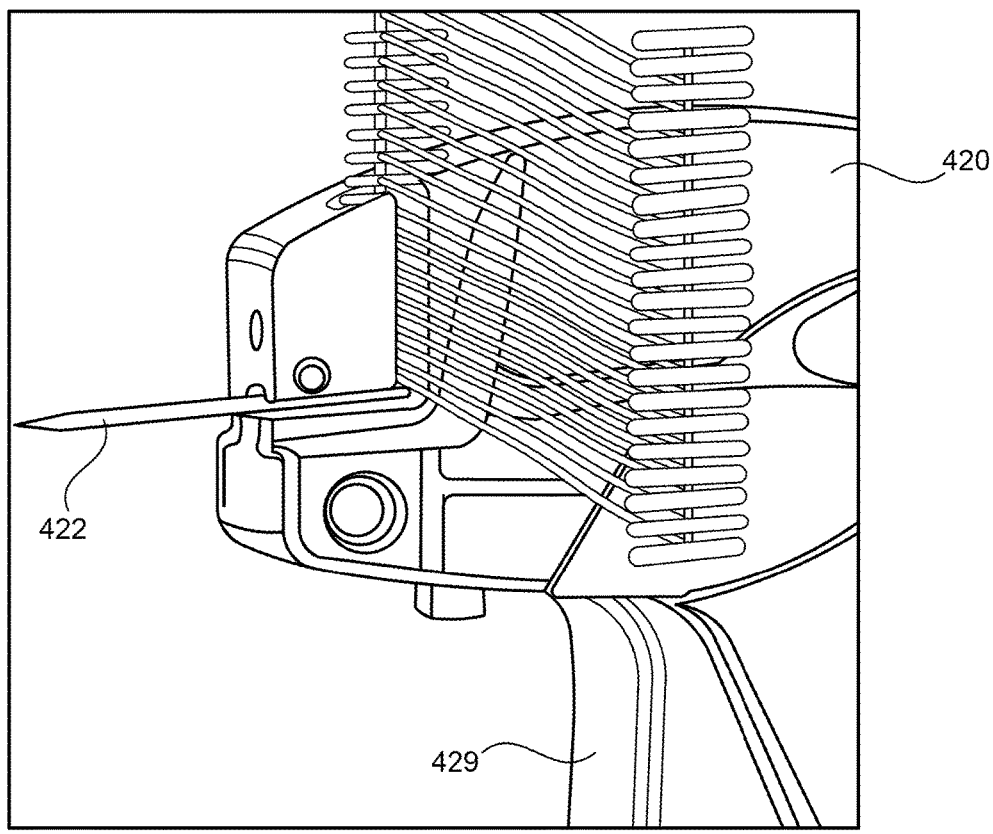
FIG. 12 is perspective view of a device for delivering an anchor of FIG. 10.

In some embodiments, the anchor or coupling mechanism 10 may be inserted into the body of the patient using an insertion device 420 as illustrated in FIG. 12. The insertion device 420 may be configured to retain the coupling mechanism 410 within a lumen defined by a needle portion 422 of the insertion device 420 while the insertion device 420 and the anchor 410 are inserted into the body of the patient. The insertion device 420 may be configured to then push or force the anchor 410 out of the lumen. For example, in the illustrated embodiment, a pusher may be moved by the operator or physician (such as by moving or actuating the actuator 429), to force or push the anchor 410 out of the lumen defined by the needle portion 422 of the delivery device 420. In some embodiments, the delivery device 420 is configured to push or force the anchor 410 from the needle portion 422 while one of the retention portions is in a collapsed or folded configuration.

In the illustrated embodiment, the delivery device 420 is configured to retain or hold more than one anchor 410. Accordingly, the delivery device and the plurality of anchors may be inserted into the body. The anchors may be placed within the body at different locations and may be placed serially without having to remove the delivery device from the body of the patient. In other embodiments, a different type of device may be used to deliver the anchor 410 into position within the body of the patient.

In some embodiments, the anchor or coupling member 410 is configured to have a limited penetration depth into the bodily tissue. For example, in some cases the bodily tissue is a vagina or a vaginal wall of a patient. In some embodiments, the anchor or coupling member 410 is configured to couple the implant to the vagina or the vaginal wall without extending through the vaginal wall into the vaginal canal of the patient.

The anchor or coupling member 410 may be formed of any type of biocompatible material.

Figure 13:
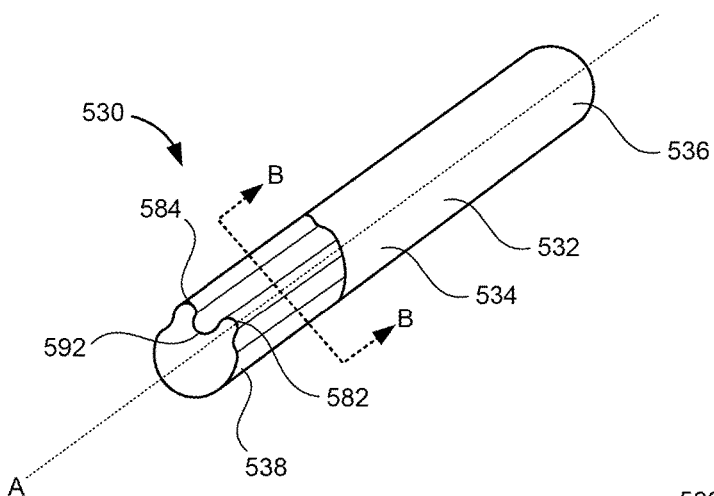
FIG. 13 is a perspective view of a manipulator according to an embodiment of the invention.
Figure 14:
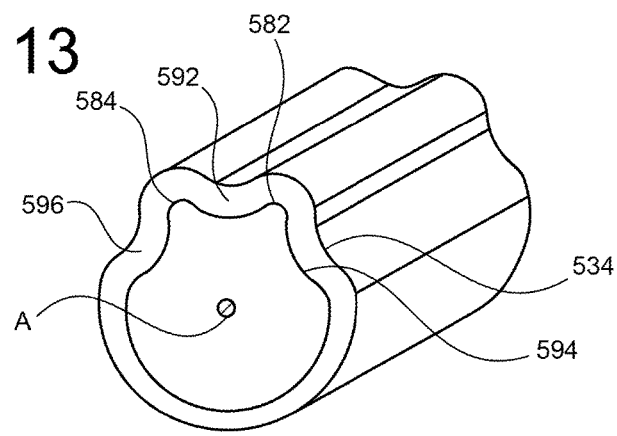
FIG. 14 is a cross-sectional view of the manipulator of FIG. 13.
Figure 15:
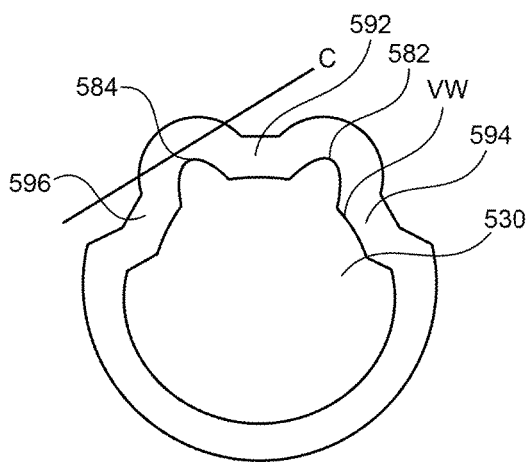
FIG. 15 is a schematic view of the manipulator of FIG. 13 disposed within a body of a patient.

FIGS. 13-15 illustrate a manipulator 530 according to an embodiment of the invention. The manipulator 530 is configured to be inserted into the body of the patient and manipulate or move bodily tissue. In some embodiments, the manipulation of the bodily tissue facilitates the placement or securement of the bodily implant within the body of the patient. For example, in some embodiments, the manipulator 530 is configured to be inserted into the body of the patient and manipulate the bodily tissue so as to facilitate the securement of the bodily implant to the bodily tissue.

The manipulator 530 includes an elongate member 532. The elongate member 532 has a proximal end portion 536 and a distal end portion 538. The elongate member has an outer surface 534 and defines a longitudinal axis A.

In the illustrated embodiment, the outer surface 534 of the manipulator 530 includes undulations or otherwise has a non-smooth surface. Specifically, in the illustrated embodiment, the outer surface 534 of the manipulator 530 includes or defines a first ridge or bump 582 and a second ridge or bump 584. The first ridge or bump 582 and the second ridge or bump 584 are disposed at the distal end portion 538 of the manipulator 530. The first ridge or bump 582 and the second ridge or bump 584 extend along the outer surface 534 of the manipulator in directions that are parallel to the longitudinal axis A of the manipulator 530. In other embodiments, the ridges or bumps may extend in directions that are not parallel to the longitudinal axis of the manipulator 530. Also, in other embodiments, the ridges or bumps may extend the entire length of the manipulator.

The outer surface 534 of the manipulator 530 includes or defines troughs or indentations 592, 594, and 596. The troughs or indentations 592, 594, and 596 are disposed at the distal end portion 538 of the manipulator 530. The troughs or indentations 592, 594, and 596 extend in directions that are parallel to the longitudinal axis A of the manipulator 530. In the illustrated embodiment, the troughs or indentations 592, 594, and 596 are disposed adjacent the ridges or bumps 582 and 584. In other embodiments, the troughs or indentations may extend in directions that are not parallel to the longitudinal axis of the manipulator 530. Also, in other embodiments, the troughs or indentations may extend the entire length of the manipulator.

FIG. 14 is a cross-sectional view of the manipulator 530 taken along line B-B of FIG. 13 (line B-B extends perpendicular to the longitudinal axis A of the manipulator 530). As best illustrated in FIG. 14, the first ridge or bump 582 and the second ridge or bump 584 extend a distance from the longitudinal axis A that is greater than other portions of the outer surface 534 of the manipulator 530. For example, the ridges or bumps extend a distance from the longitudinal axis A that is greater than the distance that the troughs or indentations extend from the longitudinal axis A.

In the illustrated embodiment, the manipulator 530 is configured to be inserted into a vagina of the patient and to manipulate the vaginal tissue or vaginal walls of the patient. Specifically, the manipulator 530 may be inserted into the vagina of the patient such that distal end portion 538 is disposed within the vagina. The proximal end portion 536 may extend from the vagina and allow the physician to control the movement of the manipulator 530. As best illustrated in FIG. 15, the vaginal wall VW of the vagina of the patient conforms to the contour or outer surface 534 of the manipulator 530. Specifically, the vaginal wall VW extends over the ridges or bumps 582 and 584 and depress or fold into the troughs or indentations 592, 594, and 596.

In some cases, such manipulation of the vagina or the vaginal wall VW facilitates the placement of the implant in a correct location with respect the vagina and the securement of the implant to the vagina or tissue proximate the vagina via the anchor. For example, a delivery tool (such as a needle) or an anchor may be inserted into the vaginal wall VW along the line C of FIG. 15 to couple the anchor to the vaginal wall VW but not extend to the vaginal canal of the patient. In some embodiments, the manipulator 530 may be inserted into that vagina of the patient and the delivery tool (or anchor) may be inserted into the body via an abdominal incision.

Figure 16:
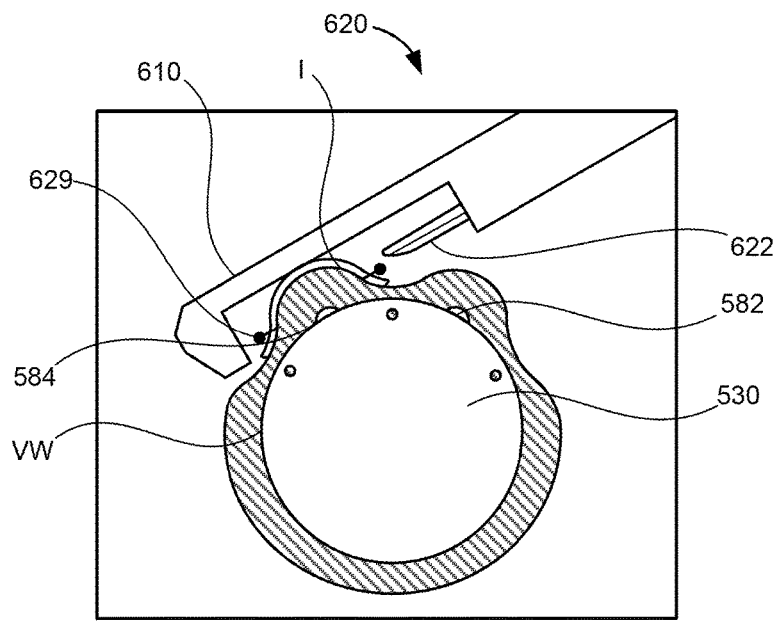
FIG. 16-18 are schematic views of a systems according to embodiments of the invention.
Figure 17:
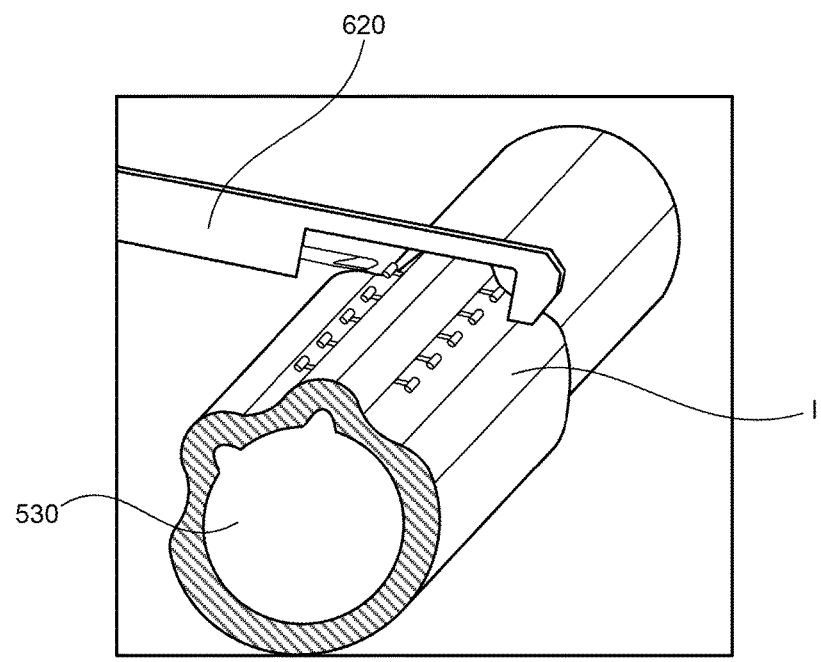

FIGS. 16 and 17 schematically illustrate a delivery tool 620 delivering an anchor to the vaginal wall VW while the manipulator 530 is disposed within the vagina of the patient. The anchor delivered by the delivery tool 620 is configured to extend through the implant I and retain the implant in place within the body of the patient. The delivery tool 620 includes a needle portion 622 that is configured to move with respect to the reminder of the delivery tool 620. For example, the needle portion 622 may be configured to move once an actuator is actuated. For example, the delivery tool may include an actuator that is configured to actuate or move the needle portion 622 with respect to the remainder of the delivery tool 620. In some embodiments, the delivery tool 620 or the needle portion of the delivery tool 620 may be configured to deliver the anchor or coupling member in a manner similar to delivery tool 420.

In the illustrated embodiment, the delivery tool 620 includes a needle guard 629. The needle guard 629 is configured to guard or protect the needle portion 622 during insertion of the delivery device 620 into the body of the patient. The needle guard 629 also functions as a depth control mechanism. Specifically, the needle guard 629 helps prevent the needle portion 622 from penetrating too deep into the bodily tissue. As best illustrated in FIG. 16, the deliver tool 620 may be disposed such that the portion of the vaginal wall that extends over one of the ridges 584 is disposed proximal the needle portion 622 and within are area defined by the needle guard 629. The needle portion 622 may then be activated to pierce the tissue and deliver the anchor 610.

While FIG. 16 illustrates delivery tool 620 being used to deliver the anchor to the bodily tissue, in other embodiments, other delivery tools may be used to deliver the anchor to the bodily tissue.

Figure 18:
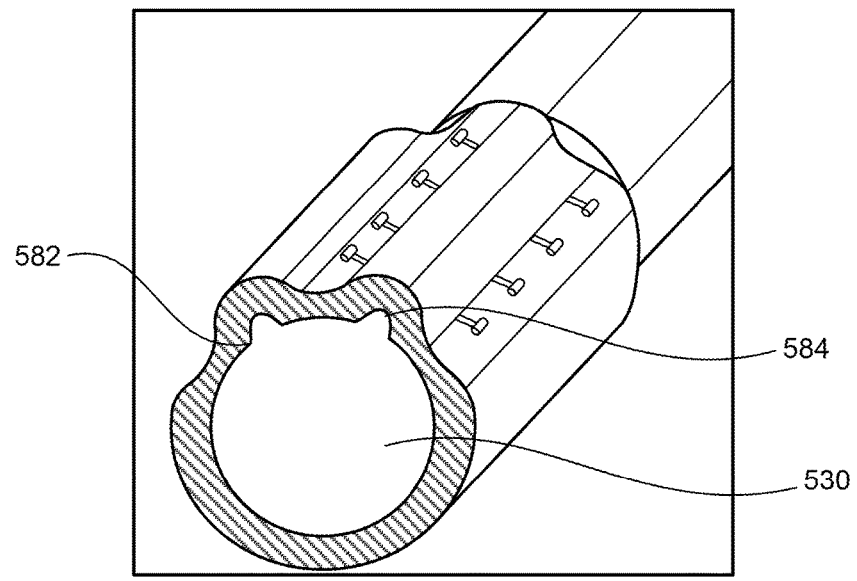

As illustrated in FIG. 17, multiple or a plurality of anchors may be coupled to the vaginal wall along the length of the ridge. As illustrated in FIG. 18, anchors may be coupled to the vaginal wall along the length of both of the ridges. In other embodiments, the manipulator may have more than two ridges. In such embodiments, anchors may be placed along the length or adjacent to any number of the ridges.

The manipulator 530 may be formed of any type of biocompatible material. The manipulator 530 may be configured to be inserted into any portion of the body of the patient and may be configured to be inserted into the body via any opening or incision.

Figure 19:
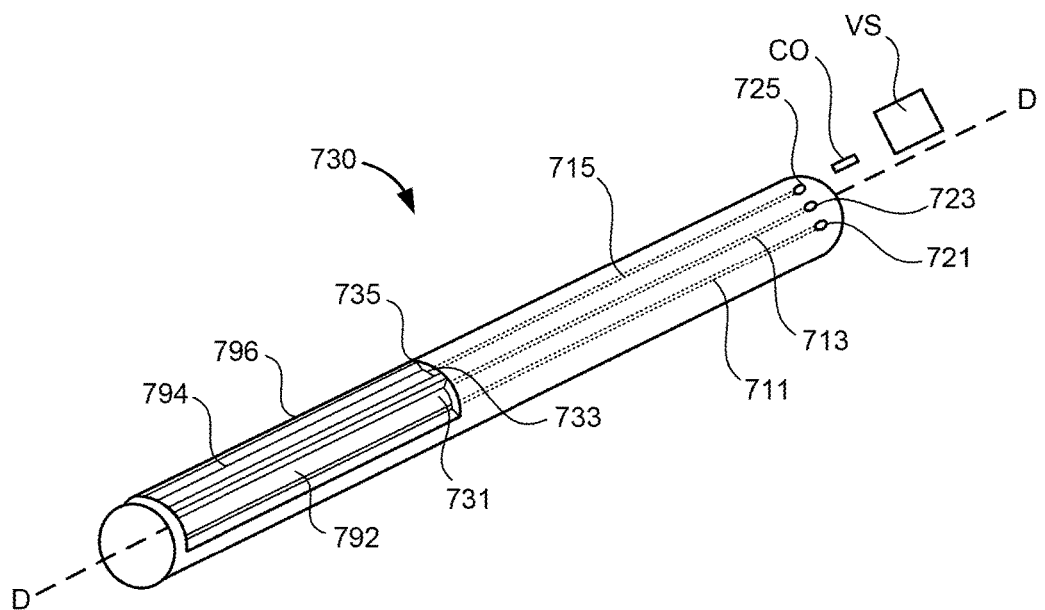
FIG. 19 is a perspective view of a manipulator according to an embodiment of the invention.
Figure 20:
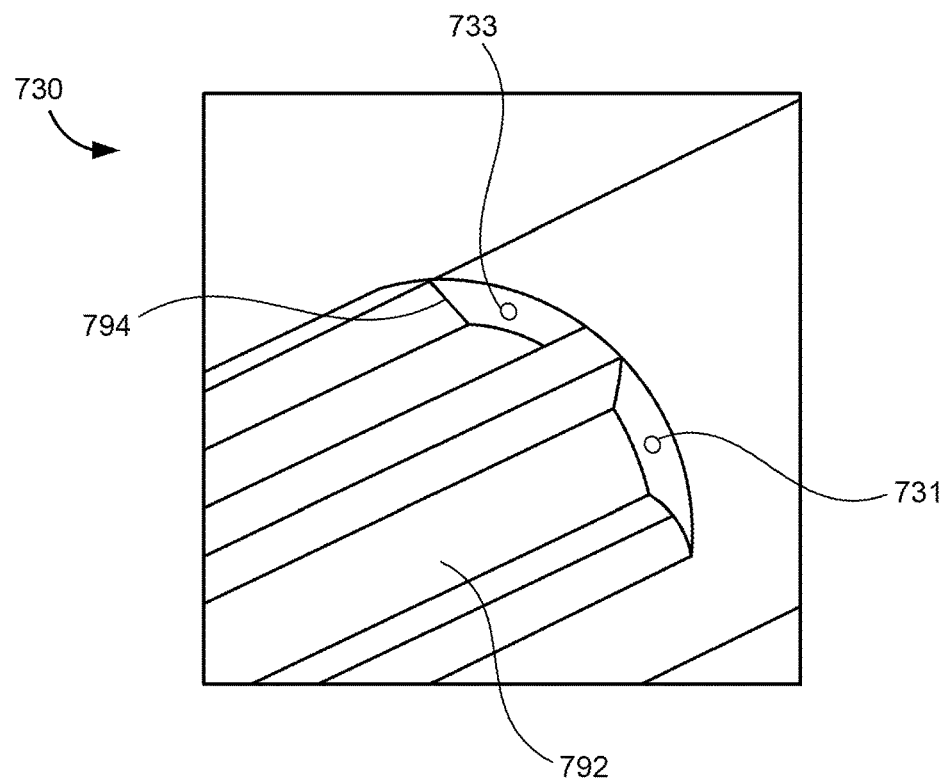
FIG. 20 is a perspective view of a portion of the manipulator of FIG. 19.

FIGS. 19 and 20 illustrate a manipulator 730 according to another embodiment of the invention. The manipulator 730 is configured to be inserted into the body of the patient and manipulate or move bodily tissue. In some embodiments, the manipulation of the bodily tissue facilitates the placement or securement of the bodily implant within the body of the patient. For example, in some embodiments, the manipulator 730 is configured to be inserted into the body of the patient and manipulate the bodily tissue so as to facilitate the securement of the bodily implant to the bodily tissue.

The manipulator 730 includes an elongate member 732. The elongate member has a proximal end portion and a distal end portion. The elongate member has an outer surface and defines a longitudinal axis D.

In the illustrated embodiment, the outer surface of the manipulator 730 includes undulations or otherwise has a non-smooth surface. Specifically, in the illustrated embodiment, the outer surface of the manipulator 730 includes or defines a first ridge or bump and a second ridge or bump. The first ridge or bump and the second ridge or bump are disposed at the distal end portion of the manipulator 730. The first ridge or bump and the second ridge or bump extend along the outer surface 734 of the manipulator in directions that are parallel to the longitudinal axis D of the manipulator 730. In other embodiments, the ridges or bumps may extend in directions that are not parallel to the longitudinal axis of the manipulator 730. Also, in other embodiments, the ridges or bumps may extend the entire length of the manipulator.

The outer surface of the manipulator 730 includes or defines troughs or indentations 792, 794, and 796. The troughs or indentations 792, 794, and 796 are disposed at the distal end portion 738 of the manipulator 730. The troughs or indentations 792, 794, and 796 extend in directions that are parallel to the longitudinal axis D of the manipulator 730. In the illustrated embodiment, the troughs or indentations 792, 794, and 796 are disposed adjacent the ridges or bumps. In other embodiments, the troughs or indentations may extend in directions that are not parallel to the longitudinal axis of the manipulator 730. Also, in other embodiments, the troughs or indentations may extend the entire length of the manipulator.

The manipulator 730 defines lumens 711, 713, and 715. The lumens 711, 713, and 715 extend from the proximal end portion of the manipulator 730 to the troughs 792, 794, and 796, respectively. Specifically, as illustrated in FIG. 19, the proximal end portion of the manipulator 730 defines openings 721, 723, and 725. The manipulator 730 also defines openings 731, 733, and 735 at locations proximate to, adjacent to, or within the troughs 792, 794, and 796. The lumens 711, 713, and 715 each extend from an opening defined by the proximal end portion of the manipulator 730 to an opening defined by the manipulator 730 near the troughs 792, 794, and 796.

The lumens are configured to be operatively coupled to a vacuum source VS. For example, a vacuum source VS or sources may be operatively coupled to the lumens via the openings defined by the manipulator 730 near the proximal end of the manipulator 730. For example, a coupling device CO may operatively couple a vacuum source VS to the lumens.

In the illustrated embodiment, the manipulator 730 is configured to be inserted into a vagina of the patient and to manipulate the vaginal tissue or vaginal walls of the patient. Specifically, the manipulator 730 may be inserted into the vagina of the patient such that distal end portion is disposed within the vagina. The proximal end portion may extend from the vagina and allow the physician to control the movement of the manipulator 730. Once the manipulator 730 is in place within the vagina the vacuum source may be activated or turned on to create a vacuum through the lumens 711, 713, and 715. In some embodiments, the vacuum may facilitate the conforming of the vaginal wall to the outer surface of the manipulator 730. Once the procedure is completed, the vacuum source may be removed or turned off and the manipulator 730 may be removed from the body of the patient.

Figure 21:
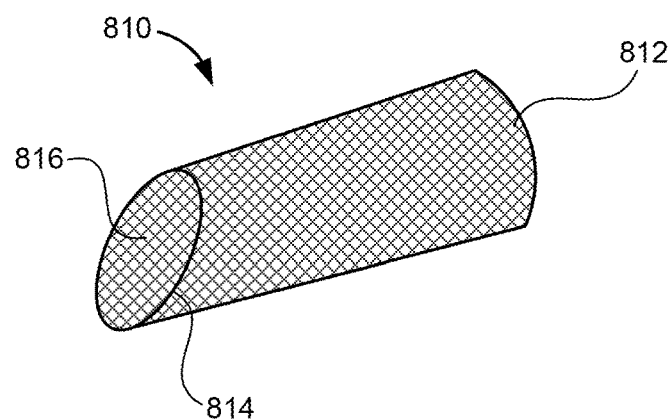
FIG. 21 is a perspective view of an implant according to an embodiment of the invention.

FIG. 21 illustrates an implant 810 that may be inserted into a body of a patient. The implant 810 has a first end portion 812 and a second end portion 814 and defines a lumen 816 that extends from the first end portion 812 to the second end portion 814. In the illustrated embodiment, the implant 810 is formed of a mesh material. In other embodiments, the implant 810 may be formed of any biocompatible material.

The implant 810 may be used in any portion of the body. In some embodiments, the implant 810 is used to provide support to a portion of the body of the patient. In some embodiments, the implant 810 is configured to be disposed within a pelvic region of the patient and is configured to provide support to a vagina of the patient. For example, as discussed in further detail below, the implant 810 may be used in a sacral colpopexy procedure.

Figure 22:
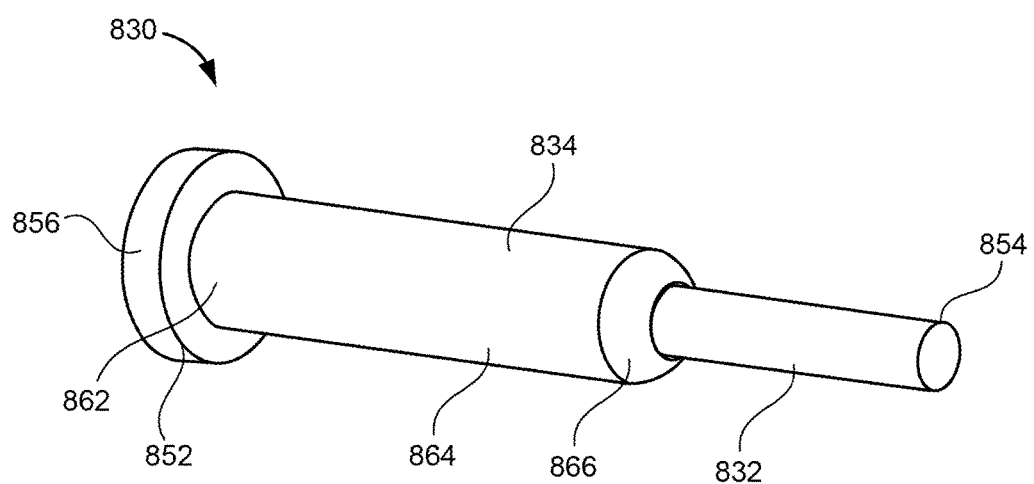
FIGS. 22 and 23 are perspective views of a manipulator according to an embodiment of the invention.
Figure 23:
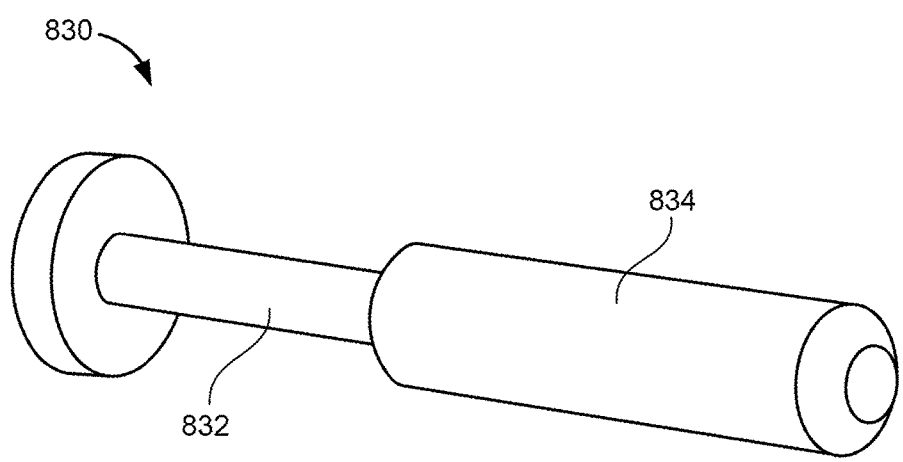

FIGS. 22 and 23 illustrate a manipulator 830 according to an embodiment of the invention. The manipulator includes a first member or portion, an elongate member 832 and a second member or portion, an expander 834. The elongate member 832 includes a proximal end portion 852 and a distal end portion 854.

The expander 834 includes a proximal end portion 862 and a distal end portion 864. The expander 834 defines a lumen that extends from the proximal end portion 862 of the expander 834 to the distal end 864 of the expander 834. The expander 834 is movably coupled to the elongate member 832. Specifically, the lumen defined by the expander 834 is configured to receive the elongate member 832 such that the expander 834 is slidably coupled to the elongate member 832.

The expander 834 is configured to slide into any number of positions with respect to the elongate member 832. The expander 834 is configured to be disposed in a retracted configuration or position (as illustrated in FIG. 22) and be moved to an extended configuration or position (as illustrated in FIG. 23).

In the illustrated embodiment, the elongate member 832 includes or defines a handle or grip portion 856. The handle or grip portion 856 is larger in diameter or width than the reminder of the elongate member.

In the illustrated embodiment, the expander 834 includes or defines a taper portion 866. The taper portion 866 tapers from a larger section on the proximal side of the taper portion 866 to a smaller side on the distal side of the taper portion. Accordingly, in some embodiments, the taper portion 866 helps facilitate the insertion or movement of the expander 834 in the body of the patient. In some embodiments, the expander includes a handle portion disposed at or near the proximal end portion 862.

Figure 24:
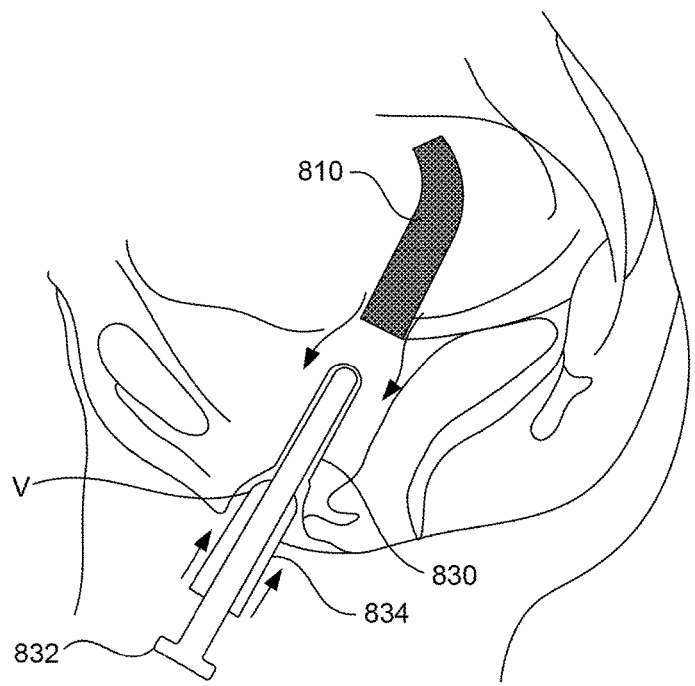
FIGS. 24-27 are schematic views of a process of using a system in accordance with an embodiment of the invention.

FIGS. 24-27 schematically illustrated a process or method for disposing an implant into a body of a patient according to an embodiment of the invention. Additionally, FIG. 28 is a flow chart that details the steps of the process or method 900. As illustrated in FIG. 24 (at 910 of FIG. 28), the manipulator 830 may be inserted into the body of the patient via the vagina V of the patient. The manipulator 830 may be inserted into the body while the manipulator 830 is in its retracted configuration or position (as shown in FIG. 22). As illustrated in FIG. 24, the implant 810 may also be inserted into the body of the patient. The implant 810 in some cases is inserted into the body via an abdominal incision.

Figure 25:
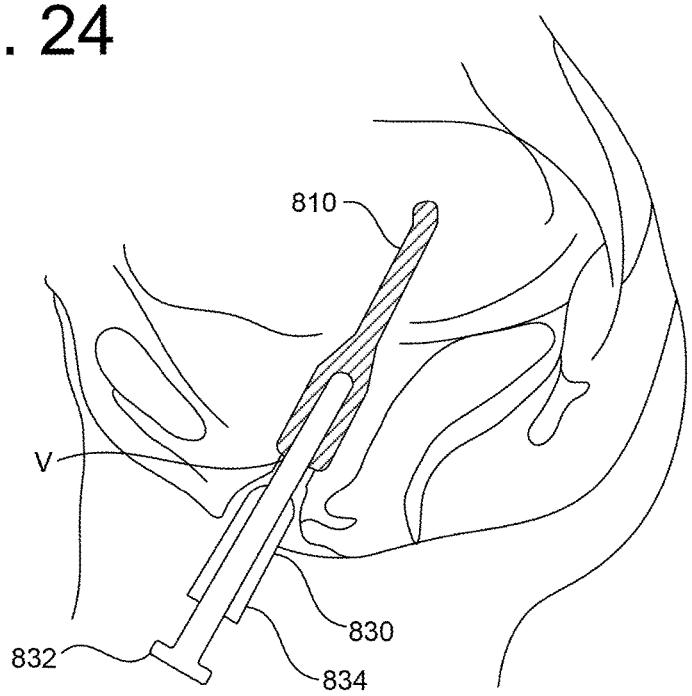

As illustrated in FIG. 25 (at 920 of FIG. 28), the implant 810 may be positioned or fit over the vagina. For example, the vagina may be placed into the lumen 816 defined by the implant 810.

Figure 26:
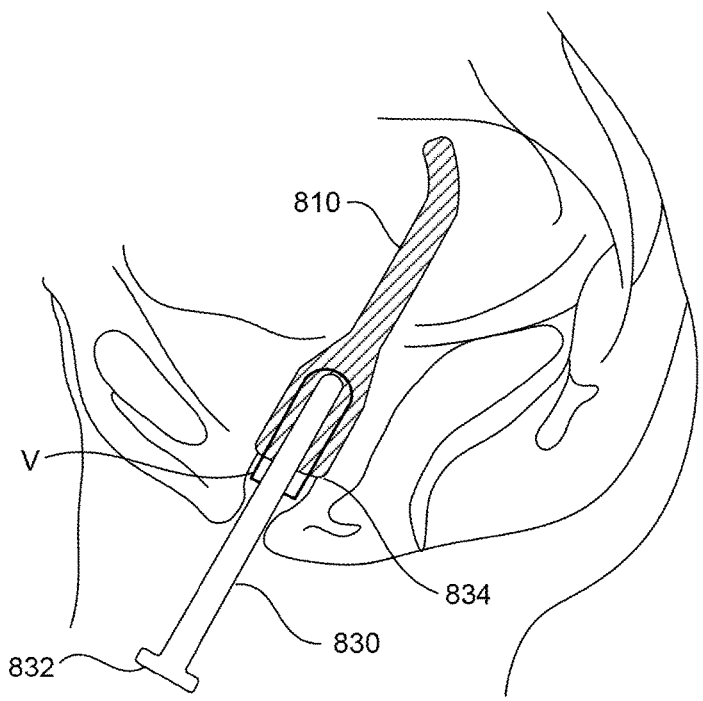

As illustrated in FIG. 26 (at 930 of FIG. 28), the expander 834 of the manipulator 830 may be moved or slid to its extended or expanded configuration (as illustrated in FIG. 23). The placement of the expander 834 within the vagina of the patent will cause the vagina to stretch or expand and will tension the implant 810 against the walls of the vagina. The implant 810 can then be secured to the vaginal walls. For example, in some embodiments, an anchor or coupling mechanism may be used to couple or secure the implant 810 to the vaginal walls. In some embodiments, the implant 810 may be coupled to the anterior vaginal wall (or tissue proximate or near the anterior vaginal wall) and may also be coupled to the posterior vaginal wall (or tissue proximate or near the posterior vaginal wall). In other embodiments, a suture or other coupling mechanism may be used. In some embodiments, the implant 810 is coupled to the vaginal walls via a laparoscopic procedure or an abdominal incision.

Figure 27:
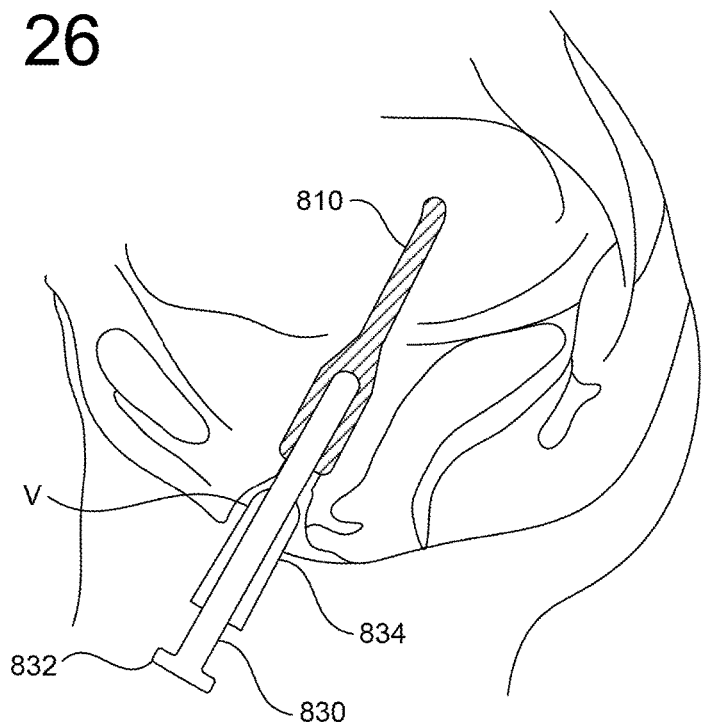
Figure 28:
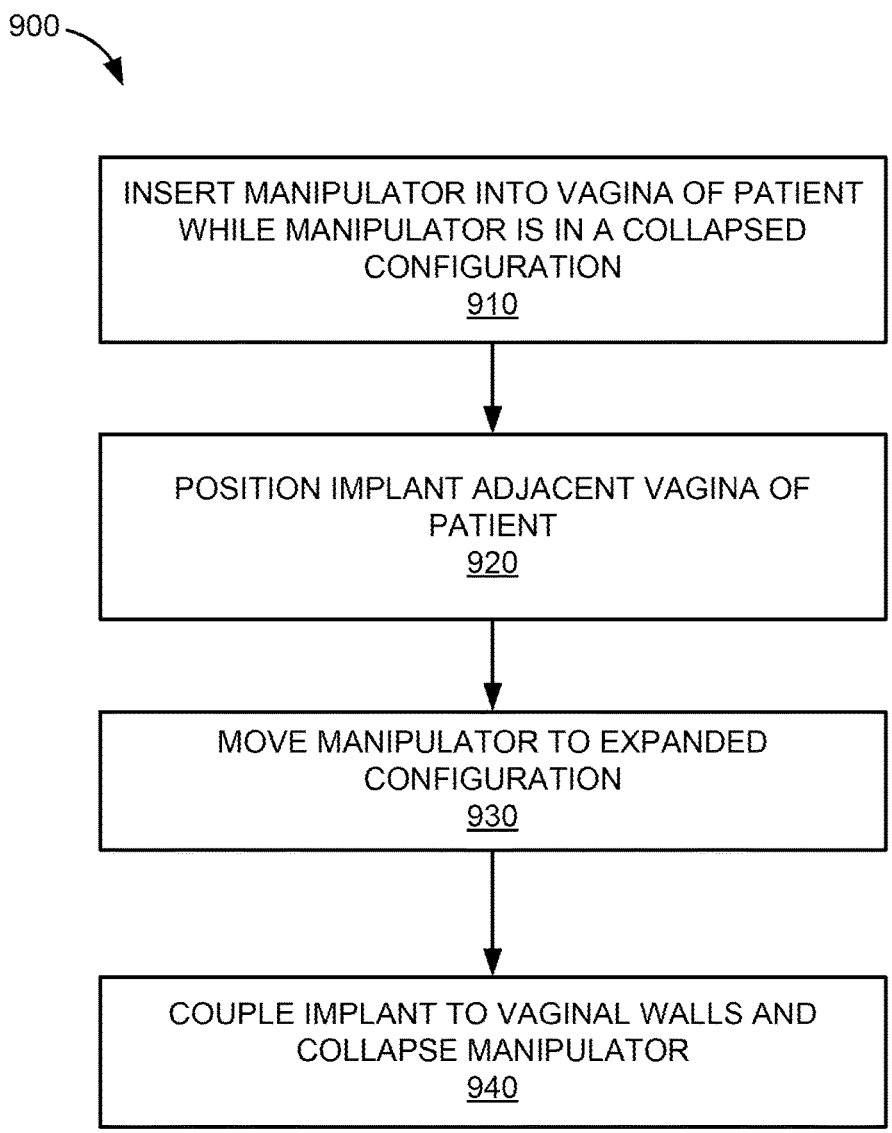
FIG. 28 is a flow chart of a method according to an embodiment of the invention.

As illustrated in FIG. 27 (at 940 of FIG. 28), the expander 834 may be moved back to its refracted configuration (as illustrated in FIG. 22). In some embodiments, a portion of the expander 834 remains outside of the body of the patient to facilitate the grasping and moving of the expander 834. In some embodiments, the implant 810 is coupled to the sacrum or tissue proximate the sacrum. The attachment of the implant 810 to the sacrum may be done via an anchor, a suture, or any other coupling mechanism. Additionally, in some embodiments, the implant 810 is cut to remove excess portions of the implant 810. Also, in some embodiments, lateral edges of the implant 810 proximate the vagina of the patient may be cut.

The manipulator 830 may then be removed from the vagina of the patient.

In some embodiments, a medical device includes an elongate member configured to be at least partially disposed within a body of a patient. The elongate member has an outer surface. The outer surface of the elongate member having a first ridge and a second ridge.

In some embodiments, the elongate member defines a longitudinal axis, the first ridge extends in a direction parallel to the longitudinal axis of the elongate member. In some embodiments, the elongate member defines a longitudinal axis, the first ridge extends in a direction parallel to the longitudinal axis of the elongate member, the second ridge extends in a direction parallel to the longitudinal axis of the elongate member.

In some embodiments, the outer surface of the elongate member has a first trough disposed on a first side of the first ridge and a second trough disposed on a second side of the first ridge. In some embodiments, the outer surface of the elongate member has a first trough disposed on a first side of the first ridge and a second trough disposed on a second side of the first ridge, the first trough extends in a direction parallel to a longitudinal axis of the elongate member.

In some embodiments, the elongate member defines a lumen configured to be operatively coupled to a vacuum source. In some embodiments, the elongate member defines a lumen that extends from a first opening defined the elongate member to a second opening defined by the elongate member, the first opening being disposed proximate a first end portion of the elongate member, the second opening being disposed proximate a trough defined by the elongate member. In some embodiments, the elongate member defines a lumen that extends from a first opening defined the elongate member to a second opening defined by the elongate member, the first opening being disposed proximate a first end portion of the elongate member, the second opening being disposed within a trough defined by the elongate member. In some embodiments, the elongate member defines a first lumen and a second lumen, the first lumen being configured to be operatively coupled to a vacuum source, the second lumen being configured to be operatively coupled to a vacuum source.

In some embodiments, the outer surface of the elongate member has a first trough disposed on a first side of the first ridge and a second trough disposed on a second side of the first ridge, the first trough extends in a direction parallel to a longitudinal axis of the elongate member, the elongate member defines a first lumen and a second lumen, the first lumen extending from a first end portion of the elongate member to a location proximate the first trough, the second lumen extending from the first end portion of the elongate member to a location proximate the second trough.

In some embodiments, a medical device includes an elongate member and an expander, the expander defining a lumen and being slidably coupled to the elongate member, the expander having a proximal end portion and a distal end portion, the distal end portion of the expander having a tapered section.

In some embodiments, the expander is configured to move from a first position on the elongate member to a second position on the elongate member.

In some embodiments, the proximal end portion of the expander includes a handle portion, a proximal end portion of the elongate member includes a handle portion. In some embodiments, the proximal end portion of the expander includes a handle portion, a proximal end portion of the elongate member includes a handle portion, the device being configured to be inserted into a body of a patient such that the handle portion of the elongate member and the handle portion of the expander are disposed outside of the body of the patient.

In some embodiments, a method of placing an implant within a body of a patient includes inserting a manipulator within a vagina of a patient; disposing the implant adjacent a vaginal wall of the patient; moving a first portion of the manipulator with respect to a second portion of the manipulator to expand the vagina of the patient; and attaching the implant to the vaginal wall of the patient.

In some embodiments, the moving includes sliding the first portion of the manipulator with respect to the second portion of the manipulator. In some embodiments, the disposing includes disposing the manipulator within the vagina of the patient such that a handle portion of the first portion of the manipulator is disposed outside of the vagina of the patient and a handle portion of the second portion of the manipulator is disposed outside of the vagina of the patient. In some embodiments, the attaching includes suturing the implant to the vaginal wall of the patient. In some embodiments, the disposing the implant adjacent the vaginal wall of the patient includes inserting a portion of the vaginal wall into a lumen defined by the implant. In some embodiments, the moving includes moving the first portion of the manipulator from a first position with respect to the second portion of the manipulator to a second position, the method further including moving the first portion of the manipulator from the second position with respect to the second portion of the manipulator to the first position; and removing the manipulator from the body of the patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device comprising:
    an elongate member configured to be at least partially disposed within a vagina of a patient, the elongate member having a distal end portion and a proximal end portion defining a longitudinal axis along a length of the elongate member, the distal end portion of the elongate member having an outer surface, the distal end portion including a first portion of the outer surface having a substantially smooth surface and a second portion of the outer surface having a first ridge and a second ridge and a first trough, a second trough and a third trough disposed at the distal end portion of the elongate member, the first ridge being disposed between the first trough and the second trough, and the second ridge being disposed between the second trough and the third trough, the second portion of the outer surface extending between the first trough and the third trough, the first ridge and the second ridge extending along the outer surface for a partial length of the elongate member such that the first ridge and the second ridge do not extend into the proximal end portion of the elongate member, the first ridge extending in a direction that is substantially away from the longitudinal axis of the elongate member.

2. The medical device of claim 1, wherein the first ridge extends in a direction parallel to the longitudinal axis of the elongate member.

3. The medical device of claim 1, wherein the first ridge extends in a direction parallel to the longitudinal axis of the elongate member, and the second ridge extends in a direction parallel to the longitudinal axis of the elongate member.

4. The medical device of claim 1, wherein the first trough is disposed on a first side of the first ridge and the second trough is disposed on a second side of the first ridge.

5. The medical device of claim 1, wherein the first trough is disposed on a first side of the first ridge and the second trough is disposed on a second side of the first ridge, the first trough extending in a direction parallel to the longitudinal axis of the elongate member.

6. The medical device of claim 1, wherein the elongate member defines a lumen configured to be operatively coupled to a vacuum source.

7. The medical device of claim 1, wherein the elongate member defines a lumen that extends from a first opening defined by the elongate member to a second opening defined by the elongate member, the first opening being disposed proximate the proximal end portion of the elongate member, the second opening being disposed proximate the first trough defined by the distal end portion of the elongate member.

8. The medical device of claim 1, wherein the elongate member defines a lumen that extends from a first opening defined by the elongate member to a second opening defined by the elongate member, the first opening being disposed proximate the proximal end portion of the elongate member, the second opening being disposed within the first trough defined by the distal end portion of the elongate member.

9. The medical device of claim 1, wherein the elongate member defines a first lumen and a second lumen, the first lumen being configured to be operatively coupled to a vacuum source, the second lumen being configured to be operatively coupled to the vacuum source.

10. The medical device of claim 1, wherein the first trough is disposed on a first side of the first ridge and the second trough is disposed on a second side of the first ridge, the first trough extends in a direction parallel to the longitudinal axis of the elongate member, the elongate member defines a first lumen and a second lumen, the first lumen extending from the proximal end portion of the elongate member to a location within the first trough, the second lumen extending from the proximal end portion of the elongate member to a location within the second trough.

11. The medical device of claim 1, wherein the first ridge extends in a direction orthogonally with respect to the longitudinal axis of the elongate member, and the second ridge extends in a direction orthogonally with respect to the longitudinal axis of the elongate member.

12. The medical device of claim 1, wherein the second ridge extends in a direction that is substantially away from the longitudinal axis of the elongate member.

13. A medical device comprising:
an elongate member configured to be at least partially disposed within a vagina of a patient, the elongate member defining a longitudinal axis along a length of the elongate member, the elongate member having a distal end portion and a proximal end portion, the distal end portion of the elongate member having an outer surface, of which a first portion of the outer surface has a substantially smooth surface and a second portion of the outer surface has a first ridge and a second ridge, the first ridge and the second ridge extending along the outer surface for a partial length of the elongate member such that the first ridge and the second ridge do not extend into the proximal end portion of the elongate member, the first ridge extending in a direction that is substantially away from the longitudinal axis of the elongate member,
wherein the distal end portion includes a first trough and a second trough, the outer surface is disposed at a first distance from the longitudinal axis, the first ridge extending a second distance from the longitudinal axis, the first trough extending a third distance from the longitudinal axis, the second distance being greater than the first distance, the third distance being less than the first distance.

14. A medical device comprising:
an elongate member configured to be at least partially disposed within a vagina of a patient, the elongate member defining a longitudinal axis along a length of the elongate member, the elongate member having a distal end portion and a proximal end portion, the distal end portion of the elongate member having an outer surface, of which a first portion of the outer surface has a substantially smooth surface and a second portion of the outer surface has a first ridge and a second ridge, the first ridge and the second ridge extending along the outer surface for a partial length of the elongate member such that the first ridge and the second ridge do not extend into the proximal end portion of the elongate member, the first ridge extending in a direction that is substantially away from the longitudinal axis of the elongate member,
wherein the distal end portion includes a first trough and a second trough, the first trough defining an opening to a first lumen that extends through the proximal end portion of the elongate member, the second trough defining an opening to a second lumen that extends through the proximal end portion of the elongate member.

* * * * *